United States Patent [19]

Hirsch et al.

[11] Patent Number: 4,927,548

[45] Date of Patent: May 22, 1990

[54] PROCESS FOR THE PRODUCTION OF BASIC SOAPS OF DIVALENT METALS IN POWDER FORM

[75] Inventors: Albrecht Hirsch, Bremerhaven; Erwin Fleischer, Schiffdorf, both of Fed. Rep. of Germany

[73] Assignee: Neynaber Chemie GmbH, Loxstedt, Fed. Rep. of Germany

[21] Appl. No.: 315,963

[22] Filed: Feb. 27, 1989

[30] Foreign Application Priority Data

Feb. 26, 1988 [DE] Fed. Rep. of Germany ....... 3806192

[51] Int. Cl.$^5$ .......................................... C10M 129/26
[52] U.S. Cl. ...................... 252/17; 260/413; 260/414; 252/367; 252/368
[58] Field of Search .......... 252/17, 368, 367; 260/413 S, 414

[56] References Cited

U.S. PATENT DOCUMENTS 4,235,794  11/1980  Rieber et al. ......................... 252/17

FOREIGN PATENT DOCUMENTS 0163395  12/1985  European Pat. Off. .
2113521   8/1983  United Kingdom .

*Primary Examiner*—Jacqueline V. Howard
*Attorney, Agent, or Firm*—Ernest G. Szoke; Wayne C. Jaeschke; Norvell E. Wisdom, Jr.

[57] ABSTRACT

Powdered basic metal soaps having a composition corresponding to the formula $(MO)_n \cdot M(RCOO)_2$, where MO represents CaO, ZnO, MgO, BaO, PbO, or a mixed oxide PbO/CaO, CaO/ZnO, BaO/CdO, or BaO/ZnO, M is one of the metals mentioned above, RCOO represents an anion of a fatty acid containing 8 to 34 carbon atoms, and n has a value of 0.2 to 2, may be obtained by reaction of powdered fatty acids with powdered metal oxides in the presence of small amounts of water, alcohol, and/or an acid at temperatures between ambient temperature and 100° C. and under a pressure not greater than ambient. Preferably, there is continuous removal of water formed during the reaction, and the reaction mixture is present as free flowing particles throughout the reaction.

7 Claims, No Drawings

PROCESS FOR THE PRODUCTION OF BASIC SOAPS OF DIVALENT METALS IN POWDER FORM

FIELD OF THE INVENTION

This invention relates to a process for the production of powdered basic metal soaps having a composition corresponding to formula (I):

$$(MO)_n \cdot M(RCOO)_2 \qquad (I)$$

in which MO represents an oxide from the group consisting of CaO, ZnO, MgO, BaO and PbO or a mixed oxide from the group consisting of PbO/CaO, CaO/ZnO, BaO/CdO and BaO/ZnO; M represents a metal or metal mixture corresponding to the oxides represented by MO; the group RCOO represents an anion of a fatty acid containing 8 to 34 carbon atoms or of a mixture of such fatty acids; and n is a number between 0.2 and 2.

Metal soaps obtainable by the process according to the invention are suitable as components of stabilizer/lubricant mixtures in the processing of halogen-containing plastics, particularly poly(vinyl chloride). When these metal soaps contain calcium as the only metallic constituent, they are also particularly suitable as additives in mixed feeds for milking cows, to improve their milk yield and milk fat content, which in turn enables better-spreading butter to be obtained.

STATEMENT OF RELATED ART

Basic lead soaps, particularly lead stearate, have hitherto been produced by a precipitation process. However, such a process is expensive and, in addition, produces a very finely divided, very dusty product.

EP-A O 163 395 and GB-A 2,113,521 describe processes for the production of feeds in which liquid or molten fatty acids are reacted with calcium oxide or calcium hydroxide in the presence of proteins, carbohydrates, and substantial amounts of water. The process of EP-A 0 163 395 requires a large plant because it is taught that the reaction mixture has to be spread out over an endless belt or the like for after-reaction and drying. It appears that the calcium soaps obtained in these processes would be difficult to convert into the form of free-flowing particles in the absence of the additives mentioned, such as proteins and carbohydrates.

An object of the present invention is to provide a process with which it is possible to obtain basic metal soaps in the form of either coarse or fine powders as desired and in compositions which, in addition, have a very much higher melting point than the corresponding neutral metal soaps.

DESCRIPTION OF THE INVENTION

Except in the operating examples, or where otherwise explicitly indicated, all numerical quantities in this description specifying amounts of materials or reaction conditions are to be understood as modified by the word "about".

The invention is a process in which powdered solid primary fatty acids having the formula RCOOH, where RCOO is as defined above, are reacted, while being mechanically mixed in a reactor, with powdered solid metal oxides or metal oxide mixtures having the formula MO, in which MO is as defined above, or with the corresponding powdered solid metal hydroxides or metal hydroxide mixtures having the formula $M(OH)_2$. These powdered solid components are used in amounts corresponding stoichiometrically to the particular example of formula (I) that is to be made and are mixed with a preferably liquid component consisting of (i) 0.1 to 5% by weight (of the total mixture) of water, ethanol, or a mixture of water and ethanol and/or (ii) 0.1 to 1% by weight of a secondary acid, and are maintained at a pressure equal to or below the ambient pressure and at such temperatures, between ambient temperature and 100° C., that the reaction mixture is present in the form of discrete, free flowing particles throughout the entire process. Preferably, water formed during the reaction that occurs during this mixing is continuously removed, optionally under a slight vacuum. It is also preferable if, on completion of the reaction, the reaction product is cooled with continued mechanical mixing to a temperature between ambient temperature and 40° C. and any significant amount of residual water or alcohol formed or otherwise present is removed, normally with the aid of a slight vacuum. Eventually, the powdered metal soaps formed are removed from the reactor.

It is preferable if the value of n in the formula for the salt made by the process is between 1 and 2.

Any powdered fatty acids of natural or synthetic origin containing from 8 to 34 carbon atoms may be converted into the corresponding basic metal soaps by the process according to the invention. Saturated fatty acids are preferably used. The process is particularly advantageous for the reaction of technical mixtures of natural, saturated fatty acids containing from 14 to 34 and more preferably from 14 to 22 carbon atoms and having a melting point above the reaction temperature of the process according to the invention. Typical examples of such fatty acids are palmitic, stearic, behenic, and montanic acids and also technical mixtures containing high percentages of the fatty acids mentioned. The secondary acid, to be added to the reaction mixture in a quantity of 0.1-1% by weight, may be any acid or mixture of acids having a first (or sole) ionization product constant of at least $10^{-5}$, for example inorganic acids, such as hydrochloric acid, phosphoric acid, and sulfuric acid, and also organic acids, such as formic acid, acetic acid, propionic acid, or the like.

In one advantageous embodiment of the invention, the reaction temperature is controlled or regulated by the heat of friction generated by the mixer.

Suitable reactors are any known mixers for the intensive mixing of free-flowing solid particles.

The invention is illustrated, but not limited, by the following operating examples. The production of basic metal soaps described in these examples was carried out at temperatures below the melting points of the fatty acids used, according to the following general procedures: The reactor used was a Waring "Mixbecher" (mixing cup) having a volume of 1000 ml and a variable-speed stirrer (300 to 2000 r.p.m.). The acids used were technical "stearic acid" (actually an approximately 1:1 mixture of stearic and palmitic acids, with a liquification point of 55° C. and an average molecular weight of 270); technical "behenic acid" (approximately 90% behenic acid, with the balance mainly arachidic and stearic acids, with a liquification point of 70° C. and an average molecular weight of 340); and technical "myristic acid" (approximately 93% myristic acid, with 2% $C_{12}$ and 5%

C$_{16}$ acids, a liquification point of 46° C., and an average molecular weight of 228).

EXAMPLE 1

Production of basic calcium stearate 108.0 g of stearic acid and 31.1 g of calcium hydroxide were introduced into the mixer and heated with stirring to 40°–45° C. After addition of 0.7 g acetic acid (0.5%, based on the mixture as a whole), there was a mildly exothermic reaction with spontaneous heating of the mixture to around 65° C. At no time during the reaction was any significant amount of liquid stearic acid present. The total stirring time was 5 minutes, a dusty powder being formed after only 2 minutes. The reaction was carried out at slightly less than atmospheric pressure (70 to 90 kilopascals pressure).

A whitish, very fine, free-flowing powder having a melting temperature of 160 to more than 250° C., a Ca content of 11.0%, an acid value of 4.0, and a residual water content of 1.8% was obtained.

EXAMPLE 2

Production of calcium behenate (20% basic)

139.9 g of behenic acid and 19.0 g of calcium hydroxide were initially introduced and mixed with stirring at 60° to 65° C. After addition of 0.8 g of acetic acid (0.5%, based on the mixture as a whole), the temperature rose to 85° C. The total stirring time was 30 minutes; a dust-like powder was present after only 2 minutes. The reaction was carried out under a slight vacuum as in Example 1.

A white, loose powder having a melting temperature of 150° C., a Ca content of 6.6%, an acid value of 2.3, and a residual moisture content of 1.5% was obtained.

EXAMPLE 3

Production of dibasic lead stearate 101.1 g of PbO (neutral) and 81.6 g of stearic acid were initially introduced and mixed at 45° C. After addition of 0.9 g of acetic acid (0.5%, based on the mixture as a whole), there was a mildly exothermic reaction accompanied by heating to around 65° C. Small lumps occasionally forming on the walls of the reactor were removed by means of a stripper. The total stirring time was 20 minutes under a slight vacuum.

A pale yellowish powder having a melting temperature of 112° to more than 250° C., a lead content of 51.0%, an acid value of 2.6, and a residual moisture content of 0.2% was obtained.

EXAMPLE 4

Production of basic calcium myristate 114.5 g of myristic acid and 38.9 g of calcium hydroxide were stirred at 35° to 40° C., and 0.3% acetic acid was added as catalyst. The mass initially underwent slight compaction but then changed into a white voluminous powder. During the reaction, the temperature rose to 70°–80° C. The total stirring time was 3 minutes. A white voluminous powder having a Ca content of 13.6%, a melting temperature of 180° to more than 250° C., and an acid value of 1.6 was obtained.

EXAMPLE 5

Production of basic calcium behenate 108.8 g of behenic acid and 24.8 g of calcium hydroxide were stirred at 60° to 70° C., followed by the addition of 0.4% of acetic acid. The total stirring time was 15 minutes. During the reaction, the temperature rose to 90° C. A whitish, fine, loose powder having a Ca content of 10.1%, a melting temperature of 140 to more than 250° C., and an acid value of 4.3 was obtained.

EXAMPLE 6

Production of basic lead stearate 100.4 g of stearic acid and 83.0 g of lead oxide were stirred at 45° C. and 0.3% of acetic acid added. After stirring for 1 minute, slight clumping occurred. After cooling for 5 minutes, stirring was continued. A pale yellowish powder having a lead content of 40.9%, a melting temperature of 114° C., and an acid value of 2.0 was obtained after 20 minutes.

EXAMPLE 7

Production of dibasic lead stearate 81.6 g of stearic acid and 101.1 g of PbO and also 1%, based on the mixture as a whole, of ethanol were mixed at 45° C. and 0.3% acetic acid added. Caking occurred on the walls of the reactor during stirring, but could be removed. After 5 minutes, the product became powdery with heating to around 65° C. Thereafter, no more caking occurred. The total stirring time was 10 minutes. A pale yellowish powder having a lead content of 51.6%, a melting temperature of 114° to more than 250° C., and an acid value of 3.9 was obtained.

EXAMPLE 8

Production of basic magnesium stearate 161.5 g of stearic acid and 27.0 g of MgO were stirred at 45° C., and 1.5% of 50% acetic acid in water was added. Slight clumping of the mixture occurred at the beginning of stirring. After about 30 minutes, a readily stirrable powder was present. A whitish powder having a Mg content of 8.0%, a melting temperature of 110° to 215° C., and an acid value of 5.5 was obtained.

EXAMPLE 9

Production of basic zinc stearate 118.1 g of stearic acid and 36.3 g of zinc oxide were stirred at 45° C., and 1.5% of 30% acetic acid was added. During stirring, caking initially occurred on the walls of the reactor, but could be removed. After 5 minutes, the mixture was readily stirrable. A dusty, whitish, slightly voluminous powder having a zinc content of 18.8%, a melting temperature of 128° C., and an acid value of 4.1 was obtained after 10 minutes.

EXAMPLE 10

Production of basic lead/calcium stearate 73.7 g of stearic acid, 76.2 g PbO and 3.6 g calcium hydroxide were stirred at 40° to 45° C. and 1% of 50% acetic acid added. The temperature rose to approximately 70° C. The total stirring time was 35 minutes. A pale yellowish powder having a melting temperature of 58° to more than 250° C., a lead content of 46.1%, a calcium content of 1.2%, and an acid value of 3.1 was obtained.

EXAMPLE 11

Production of basic calcium/zinc stearate 145.3 g of stearic acid, 26.6 g of calcium hydroxide and 14.6 g of zinc oxide were mixed together at 40° to 45° C. and 1% of 50% acetic acid added. The reaction began after stirring for 2 minutes. The temperature rose to approximately 75° C. in 15 minutes. The total stirring time was 45 minutes. A whitish, loose powder having a melting temperature of 155° to more than 250° C., a calcium content of 7.6%, a zinc content of 6.5%, and an acid value of 2.1 was obtained.

EXAMPLE 12

Production of basic barium/zinc stearate 123.2 g of stearic acid, the stoichiometric equivalent of 59.6 g of barium hydroxide (actually used in the form of barium hydroxide monohydrate) and 14.8 g of zinc oxide were mixed together at 40° to 45° C., and 1% of 50% acetic acid was added. The temperature rose to 65° C. during the reaction. A whitish, loose powder having a melting temperature of 104° to more than 250° C., a barium content of 20.5%, a zinc content of 6.6%, and an acid value of 2.4 was obtained after stirring for 35 minutes.

EXAMPLE 13

Production of basic barium/cadmium stearate 117.6 g of stearic acid, the stoichiometric equivalent of 71.3 g of barium hydroxide (as monohydrate) and 14.0 g cadmium hydroxide were mixed at 40° to 45° C., and 1% of 50% acetic acid was added. The total stirring time was 35 minutes, the temperature rising to 65° C. A whitish, loose, free-flowing powder having a melting temperature of 106° to more than 200° C., a barium content of 22.8%, a cadmium content of 6.3%, and an acid value of 1.9 was obtained.

What is claimed is:

1. A process for the production of powdered basic metal soaps having a composition corresponding to the formula $(MO)_n \cdot M(RCOO)_2$, wherein MO represents a metal oxide selected from the group consisting of CaO, ZnO, MgO, BaO, and PbO, or a mixed oxide selected from the group consisting of PbO/CaO, CaO/ZnO, BaO/CdO, and BaO/ZnO; M represents a divalent metal cation or mixture of metal cations corresponding to the metal content of MO; the group RCOO represents the anions of a fatty acid containing 8 to 34 carbon atoms or of a mixture of such fatty acids; and n has a value of 0.2 to 2; said process comprising mechanically mixing in a reactor:

(a) powdered solid fatty acids having the formula RCOOH, in which RCOO is as defined above;
   (b) powdered metal oxides or metal oxide mixtures having the formula MO, or the corresponding powdered metal hydroxides or metal hydroxide mixtures; and
   (c) a component selected from the group consisting of:
      (i) about 0.1 to about 5% by weight of water, ethanol, or a mixture of water and ethanol;
      (ii) about 0.1 to about 1% by weight of a secondary acid having a first ionization product constant of at least $10^{-5}$; and
      (iii) both (i) and (ii),
      said % by weight being referred to the combined total weight of components (a), (b), and (c) of the mixture;
   the relative amounts of components (a) and (b) being such as to provide after reaction the proper stoichiometric amounts corresponding to said formula $(MO)_n \cdot M(RCOO)_2$; said mixing being performed at a temperature between ambient temperature and about 100° C. and under a pressure not greater than the ambient pressure; the reaction mixture being present in the form of discrete, free-flowing particles throughout the entire process.

2. A process according to claim 1, wherein the value of n is between 1 and 2.

3. A process according to claim 1, additionally comprising continuously removing from said reactor water formed by chemical reaction during said mixing.

4. A process according to claim 1, additionally comprising cooling the reaction product, with continued mechanical mixing, to a temperature between ambient temperature and 40° C. and removing any residual water or alcohol present by exposure to partial vacuum, before removing the reaction product from said reactor.

5. A process according to claim 1, wherein the reaction temperature is regulated by the heat of friction generated by the mixer.

6. A process according to claim 1, wherein the fatty acid used is a mixture of natural fatty acids containing 14 to 34 carbon atoms and having a melting point above the reaction temperature.

7. A process according to claim 1, wherein the fatty acid used is a mixture of naturally derived fatty acids containing about 14 to about 22 carbon atoms.

* * * * *